United States Patent [19]

Schneider et al.

[11] Patent Number: 4,869,729

[45] Date of Patent: Sep. 26, 1989

[54] APPARATUS FOR METHANE PRODUCTION

[76] Inventors: Richard T. Schneider, 17 Alachua Highlands, Alachua, Fla. 32615; Frederick A. Hauck, 2 Grandin Ter., Cincinnati, Ohio 45208

[21] Appl. No.: 54,529

[22] Filed: May 27, 1987

[51] Int. Cl.[4] .............................. B01J 7/00; B01J 8/38
[52] U.S. Cl. ........................................ 48/77; 422/139; 422/145; 422/209
[58] Field of Search .................. 48/77, 61, 66, 68; 585/733; 423/439, 440; 422/139, 142, 145, 147, 209

[56] References Cited

U.S. PATENT DOCUMENTS

| | | | |
|---|---|---|---|
| 1,219,797 | 3/1917 | Barnett et al. | |
| 2,640,760 | 6/1953 | Heim | 423/439 |
| 2,866,697 | 12/1958 | Elliott | 423/440 |
| 3,811,916 | 5/1974 | Russell et al. | 423/439 |
| 4,009,219 | 2/1977 | Tamers | 260/673 |
| 4,137,295 | 1/1979 | Tamers | 423/439 |
| 4,183,208 | 1/1980 | Horgan et al. | 48/77 |
| 4,184,852 | 1/1980 | Russ | 48/202 |
| 4,310,334 | 1/1982 | Waldron | 585/733 |
| 4,317,659 | 3/1982 | Down | 48/209 |
| 4,401,440 | 8/1983 | Alink | 48/61 |

Primary Examiner—Peter Kratz
Attorney, Agent, or Firm—Frost & Jacobs

[57] ABSTRACT

A method and apparatus for producing methane by hydrolysis of aluminum carbide, the aluminum carbide being formed by reduction of aluminum hydroxide/aluminum oxide with carbon derived from low grade coal in the presence of a catalyst at a temperature of at least 1250° C. The hydrolysis of aluminum carbide in the presence of an acid catalyst forms aluminum hydroxide and methane, and the aluminum hydroxide, along with admixed impurities, is returned to the reducing step.

10 Claims, 2 Drawing Sheets ered. The formation of carbides is carried out at a temperature of 1400° to 2200° F. (about 760° to 1205° C.), and the hydrolysis reactor is maintained at a maximum temperature of 350° F. (about 175° C.).

APPARATUS FOR METHANE PRODUCTION

BACKGROUND OF THE INVENTION

This invention relates to a method and apparatus for producing methane by hydrolysis of aluminum carbide. More particularly, aluminum hydroxide and/or aluminum oxide is reduced with carbon to form aluminum carbide which is hydrolyzed to form methane and aluminum hydroxide, and the aluminum hydroxide is recycled to the reducing step. Energy for the reduction step is supplied by combustion of low grade, and hence low cost, coal.

The prior art has disclosed the production of hydrocarbons, which may comprise methane, by hydrolysis of carbides of two or more metallic elements, and reformation of the carbides by reacting the recovered metallic elements with carbon which may be derived from coal.

U.S. Pat. No. 4,184,852, to J. J. Russ, discloses a method for making hydrocarbons containing at least about 85% methane by reacting water with metallic carbides which comprise at least one metastable carbide-forming metal and at least one stable carbide-forming metal. The hydroxides and oxides of the metals are recovered and used to make additional metal carbides. The use of both metastable and stable metal carbides is stated to be essential. Exemplary metastable carbide-forming elements include cadmium, zinc, barium, copper, zirconium, titanium, chromium, iron and lead. Stable carbide-forming elements include aluminum, manganese, calcium, magnesium beryllium and boron. Carbon to form the carbides may be obtained from coal which may contain sulfur. Most of the sulfur is stated to be removable as a slag, while the remaining sulfur is in the form of hydrogen sulfide which is removed by scrubbing the hydrocarbons produced during formation of the metal carbides. The formation of carbides is carried out at a temperature of 1400° to 2200° F. (about 760° to 1205° C.), and the hydrolysis reactor is maintained at a maximum temperature of 350° F. (about 175° C.).

The Russ patent recognizes that the overall consumption of energy used to produce hydrocarbons is less than the energy value of the hydrocarbons produced. This is apparently based on a statement in the patent that stable carbide-forming elements give off energy upon formation of carbides, whereas metastable carbide-forming elements absorb energy upon formation of carbides. This is inconsistent with the fact that carbide formation of the exemplary stable elements is an endothermic reaction.

U.S. Pat. No. 4,310,334, to R. D. Waldron, discloses a process for producing hydrocarbons by hydrolysis of carbides of at least iron and manganese. Preferably a reactive metal such as calcium, magnesium, zinc and/or aluminum is also used. Alternatively, chromium, vanadium, or rare earth metals may be substituted partially. According to the patentee, aluminum carbide is not efficient in the production of synthetic fuel due to a low "net heat ratio", defined as "the ratio of heat of combustion of fuel gases produced to the heat of combustion of the carbide". There appears to be no definition in this patent of the term "heat of combustion of the carbide". Hence, the net heat ratio is believed to be a questionable criterion for the efficiency of the process. The mixed metallic carbides are formed in a synthesizer at a temperature of 1600° to 2400° F.

Waldron conducts the hydrolysis reaction in a conversion chamber maintained at 250° to 600° F., a range in which the temperature is high enough that most metal hydroxides will be dehydrated "and low enough that unwanted vapors, such as sulfur dioxide, hydrogen sulfide, etc., can be readily removed." Heat of reaction is used to generate steam in a heat exchanger "for use elsewhere."

Other U.S. patents relating to hydrocarbon production by hydrolysis of metallic carbides include 4,009,219; and 4,317,659. An early disclosure of production of aluminum carbide is contained in U.S. Pat. No. 1,219,797.

While the broad concept of production of hydrocarbons by hydrolysis of metal carbides is well known, the prior art discussed above clearly teaches away from the use of aluminum carbide by itself as the metal carbide in the hydrolysis reaction. For reasons set forth in detail hereinafter, the present process avoids the alleged undesirability of using aluminum carbide as the sole metallic carbide.

SUMMARY OF THE INVENTION

It is an object of the invention to provide a process for production of methane utilizing aluminum carbide, wherein the energy value of the hydrocarbon gases produced is substantially increased, in comparison to the use of carbides of more than one metal.

It is a further object to provide a method of producing methane wherein sulfur-containing coal is used without the necessity of scrubbing the hydrocarbon gases produced.

According to the invention there is provided a process of producing methane which comprises forming aluminum carbide by reducing aluminum hydroxide/aluminum oxide with excess carbon derived from coal at a temperature of at least 1250° C. in the presence of a catalyst, quenching the aluminum carbide together with impurities admixed therein, hydrolyzing the aluminum carbide in the presence of an acid catalyst to form aluminum hydroxide and a hydrocarbon gas consisting essentially of methane, and returning the aluminum hydroxide and admixed impurities to the reducing step for forming additional aluminum carbide.

Although the formation of aluminum carbide from aluminum hydroxide and/or oxide and carbon is strongly endothermic, the hydrolysis of aluminum carbide is exothermic, and can partially balance the energy requirements.

The invention further provides apparatus for producing methane from aluminum hydroxide/aluminum oxide and coal, comprising means for supplying crushed coal; means for mixing crushed coal, aluminum hydroxide and a catalyst in predetermined proportions; a reduction furnace having an inlet to receive the mixture of crushed coal, aluminum hydroxide and catalyst, the furnace including means for fluidizing and heating the mixture to a temperature of at least 1250° C. and means for collecting aluminum carbide formed therein; a quench chamber in communication with said furnace for receiving and cooling the aluminum carbide; a hydrolysis chamber in communication with the quench chamber for receiving the aluminum carbide after quenching thereof, the hydrolysis chamber having an inlet for water and/or steam, an outlet for withdrawal of methane-containing gas product, and an outlet for withdrawal of aluminum hydroxide and impurities in the form of a sludge; and means for recycling aluminum hydroxide from the hydrolysis chamber to the mixing means.

DETAILED DESCRIPTION OF THE INVENTION

Aluminum hydroxide is convertible into aluminum carbide in accordance with the equations:

$$2Al(OH)_3 \rightarrow Al_2O_3 + 3H_2O \tag{1}$$

$$2Al_2O_3 + 9C \rightarrow Al_4C_3 + 6CO \tag{2}$$

Aluminum carbide is hydrolyzed by water and/or steam in the presence of an acid catalyst in accordance with the equation:

$$Al_4C_3 + 12H_2O \rightarrow 3CH_4 + 4Al(OH)_3 \tag{3}$$

It is apparent from equation (3) that three moles of methane are produced from each mole of aluminum carbide. The potential heat value of the gaseous hydrocarbon product is thus substantially greater than that resulting from hydrolysis of metals such as iron, manganese, magnesium and calcium, wherein only one or two moles of hydrocarbon are formed from each mole of carbide. Moreover, magnesium carbide and calcium carbide form acetylene or acetylene derivatives upon hydrolysis, which are hazardous to handle.

Since the energy requirements for aluminum carbide formation are supplied at low cost, and since the potential heat value of methane produced by hydrolysis of aluminum carbide is relatively high, it is apparent that the efficiency and cost of the method of the present invention are superior to the prior art methods requiring two or more metallic carbides. The net heat ratios disclosed in the above-mentioned Waldron patent are not a valid measure of the overall efficiency of a process of the present type.

Aluminum hydroxide is formed in the hydrolysis step. As indicated above, the aluminum hydroxide is recycled to the reduction step. Since aluminum hydroxide transforms to $Al_2O_3 \cdot 2H_2O$ at 235° C. or to $Al_2O_3$ at 300° C., it is evident that the compound actually undergoing reduction is primarily aluminum oxide since the reduction step is conducted at a temperature far above 300° C. For this reason the appended claims refer to reducing aluminum hydroxide/aluminum oxide, in order to indicate the in situ transformation of the starting material (aluminum hydroxide) to aluminum oxide in the reduction chamber or furnace.

The reduction reaction is conducted at a temperature of at least 1250° C. but below the melting point of pure aluminum oxide (about 2050° C.).

The hydrolysis step is carried out in a reaction chamber maintained at a temperature of about 150° to about 315° C. This retains sulfur and other impurities in non-volatile form. Since the reaction temperature may reach about 600° C., it is evident that a substantial amount of heat may be transferred from the hydrolysis reaction chamber for generation of steam or other uses.

Figure 1:
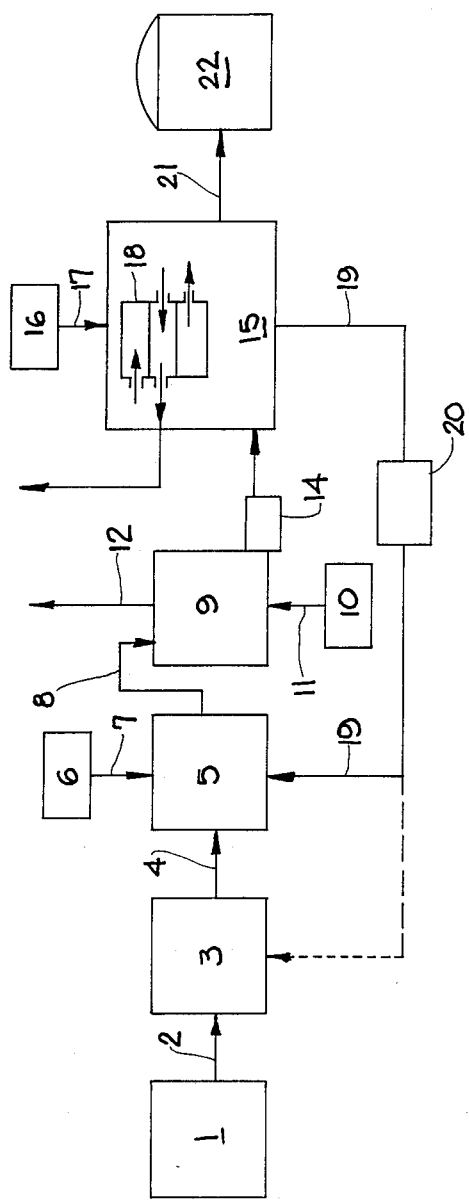
FIG. 1 is a flow diagram embodying the invention.

Referring to FIG. 1, coal (which may be low grade, sulfur containing coal) is conducted from a storage facility 1 by a conveyor means 2 to a crusher 3, where it is comminuted to a particle size small enough to permit fluidization, e.g. −100 mesh U.S. Standard Screen Scale. The coal is then conducted through line 4 to a mixer 5, where it is mixed uniformly with comminuted aluminum hydroxide recycled through a line 19 and a crusher 20 from a hydrolysis chamber 15. Alternatively, recycled aluminum hydroxide may be conducted to crusher 3, thus eliminating the need for crusher 20. Make-up aluminum hydroxide or oxide in comminuted form may also be added to mixer 5 if needed, from a supply source 6 through line 7. The particle size should be about the same as that of the crushed coal. A stoichiometric excess of coal is maintained in mixer 5. The mixture of coal and aluminum hydroxide is then passed through line 8 to a reduction furnace indicated generally at 9. Additional low grade coal is supplied to a pyrolyzer 10 where it is pyrolyzed, and the volatile gases are introduced directly into reduction furnace 9 through line 11, for combustion as described in detail below. Combustion exhaust gases are discharged through line 12.

From furnace 9, the molten reaction products are conducted to a quench chamber 14 where the temperature is reduced to about 300° C. The products are then passed to enclosed hydrolysis chamber 15. Water from a supply source 16 is introduced through line 17 as a spray into chamber 15. As indicated above, the hydrolysis reaction may reach a temperature of about 600° C. Hydrolysis chamber 15 is maintained at a temperature of about 150° to about 315° C. by means of a heat exchanger 18 which transfers heat to a steam boiler or other energy generator (not shown).

Although not shown in FIG. 1, it will be evident that the heat withdrawn from the reaction products in quench chamber 14 may also be used to generate steam, by means of a heat exchanger.

In hydrolysis chamber 15, the aluminum carbide reacts with water in the presence of an acid catalyst, such as hydrochloric acid, (introduced with water through line 17) to produce methane and aluminum hydroxide. The methane gas product formed in chamber 15 is withdrawn through a line 21 for cooling, condensation of water vapor present therein and storage in a tank 22.

The process is conducted at or near atmospheric pressure. Any pressure build-up in the system can be relieved by appropriate means, not shown.

It is well known that a liquid-liquid reaction proceeds more efficiently than a solid-solid or solid-liquid reaction. This is also applicable to the carbon-aluminum oxide reaction of the present process. In order to lower the melting point of aluminum oxide, it is a feature of the invention to add to the powdered coal and aluminum hydroxide in the mixer 5 a relatively small amount of powdered metallic aluminum to act as a catalyst. The presence of impurities in the aluminum hydroxide recycled from the hydrolysis step also lowers the melting point of the aluminum oxide formed in situ in the reduction furnace. Although precise information has not yet been obtained, it appears that the metallic aluminum (which melts at about 660° C.) and impurities in the recycled aluminum hydroxide coact to cause the formation of a molten pool in which aluminum oxide also melts (or dissolves) at a temperature as low as about 1250° C. The solubility of carbon in aluminum oxide at 1250° C. or higher is not known, but it appears to be sufficient to cause the reduction reaction to proceed at reasonable speed in the process of the present invention. Good results are obtained at a temperature of about 1880° C.

Figure 2:
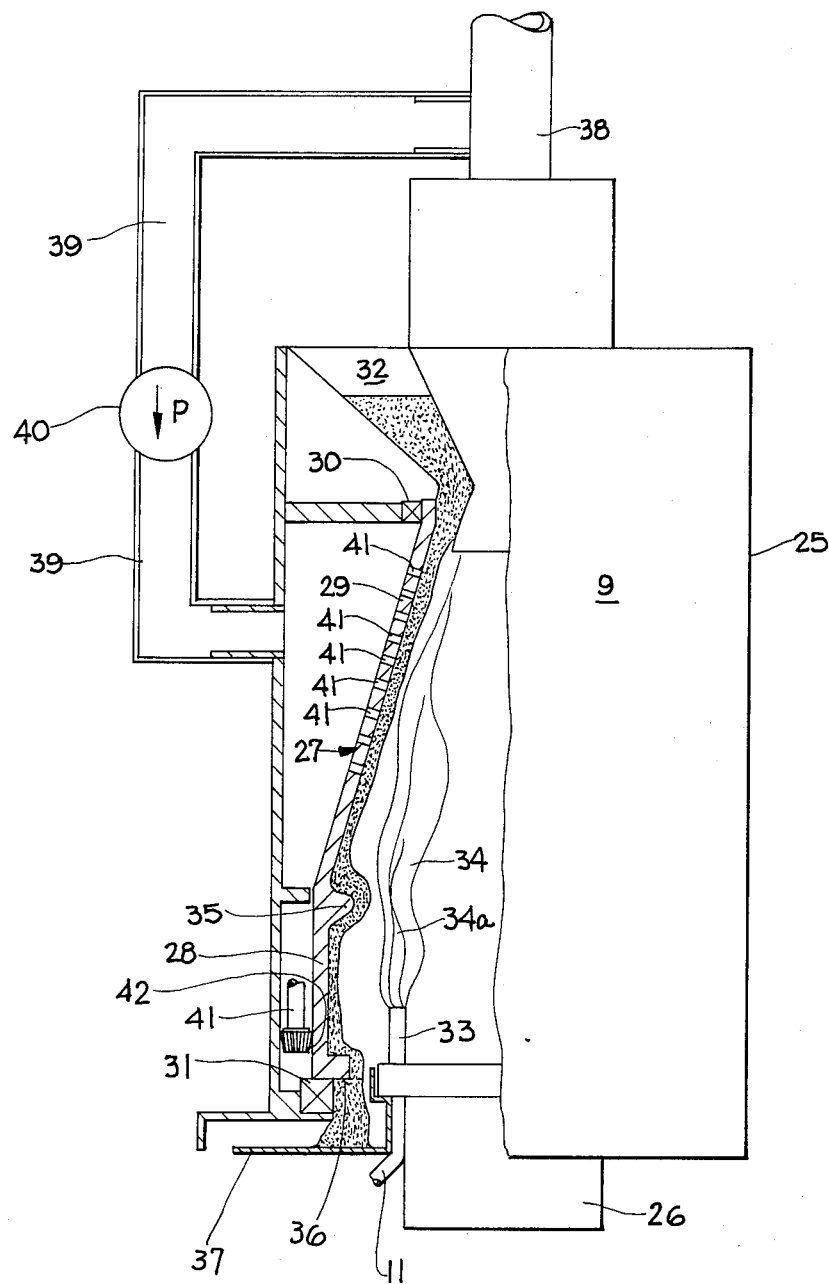
FIG. 2 is a schematic sectional view of a reduction furnace of the invention.

The reduction furnace 9 is shown in detail in FIG. 2. As illustrated schematically and partially in vertical section furnace 9 includes an outer cylindrical housing 25 supported on a base plate 26. Within housing 25 a rotating, partially fluidized bed unit is provided, indicated generally at 27. Unit 27 comprises a lower cylindrical section 28 lined with firebrick and an upper foraminous section 29 of frusto-conical configuration. Unit 27 is supported by upper and lower ring bearings of the roller type, indicated at 30 and 31, respectively, which act as pressure seals. The pressure seals are atmospheric and are provided because the unit 27 rotates at relatively low RPM in a carbon monoxide and carbon dioxide containing atmosphere, as described in more detail hereinafter.

At the upper end of furnace 9 a charging hopper or inlet 32 is provided into which a mixture of particulate coal dust, aluminum hydroxide and catalyst is introduced from mixer 5 (FIG. 1). This charge passes downwardly into the rotating conical portion 29 of unit 27 and is held against the interior wall thereof by centrifugal force. As described above the charge mixture introduced through line 8 (FIG. 1) into hopper 32 contains a stoichiometric excess of carbon in the form of coal.

In the lower part of furnace 9 a stationary ring of burners is provided as shown at 33, and the burners are supplied with a combustible mixture of air and volatilized organic gases, through line 11, from pyrolyzer 10 (FIG. 1). A stationary ring of flames 34 from burners 33 extends upwardly inside the furnace and impinges upon the descending charge of coal and aluminum hydroxide.

Adjacent the uppermost end of the cylindrical section 28 of unit 27 an inwardly projecting transition rim 35 is provided. At the lowermost end of cylindrical section 28 an inwardly projecting weir is provided as indicated at 36.

The flames 34 are so regulated that the hot core thereof extends upwardly to the transition rim 35, as indicated at 34a. Oxygen enrichment of the flames may be utilized in order to ensure a sufficiently high flame temperature in the core region. The upper portions of the flames act to preheat the descending charge above the transition rim 35. As the charge moves downwardly from transition rim 35 toward the weir 36, the temperature of the charge reaches at least 1250° C., and it becomes molten. The maximum temperature, which may slightly exceed 1800° C., is reached adjacent the weir 36, where most of the reaction resulting in aluminum carbide formation occurs. Molten aluminum carbide forms a pool which flows over the weir 36 and is spattered into a receiver 37 from which it is conducted into quench chamber 14 (FIG. 1.).

The aluminum carbide reaction forms carbon monoxide (Reaction 2 above) which is conducted upwardly inside rotating unit 27 along with carbon dioxide resulting from combustion of the volatilized gases supplied to burners 34. These hot gases also preheat the charge before being withdrawn from a flue 38 at the top of housing 25. A portion of these exhaust gases is diverted from flue 38 through conduit 39, passed through a pump or compressor 40 and reintroduced into the conical section 29 through a plurality of small apertures 41 in section 29. This creates a fluidizing effect on the descending charge which, along with centrifugal forces acting thereon, provides a vigorous mixing and shaking action.

The carbon monoxide-carbon dioxide atmosphere present within rotating unit 27 and surrounding the conical portion 29 thereof is reducing and thus inhibits formation of sulfur oxides and nitrogen oxides for reasons described hereinafter.

The remaining carbon monoxide-containing exhaust gas withdrawn through flue 38 is utilized by combustion, e.g. in a conventional steam tube boiler, to generate electricity which may be used to drive compressor 40 and an air compressor (not shown) for the gases supplied to burners 33.

Section 27 is rotated by any conventional means, such as bevel gears 41 and 42, a worm gear drive or the like. The speed of rotation may vary between about 100 to 500 RPM. The angle of conical section 27 is so selected that the charge will move downwardly along the inner wall at a desired rate, and this can be controlled by the speed of rotation of unit 27.

Fluidization of the charge in the conical section 29 is relied upon to prevent caking of the charge particles and to control downward movement. Fludization is not carried out in the lower section since the fludizing gas would cool the charge.

The weir 36 ensures that a pool of molten charge is maintained on the inner wall of furnace section 28, at a transition zone where the charge particles are reacting. Substantially all the particles are forced to rise up to the surface where reaction occurs at the hottest part of the furnace. Hence only reacted particles pass over the weir. Mass throughput is controlled by this weir in accordance with the equations:

$$\text{mass throughput (kg/hr)} = 2\pi rd(h/t)(\rho c - \rho im)\epsilon$$

wherein $\pi = 22/7$, r is the radius of the weir, d is the thickness of the charge over the rim of the weir, h is the height of the rim, t is the time required to pass over the rim, $\rho c$ is the average density of the coal and aluminum oxide, $\rho im$ is the density of the impurities present, and $\epsilon$ is the conversion efficiency of the furnace.

Any unreacted impurities will stay in solution or in suspension during the reaction and end up as impurities in the solidified aluminum carbide after cooling. In most instances, the impurities are trapped in the residue of the hydrolysis step in the form of a sludge.

Molten aluminum oxide and aluminum carbide pools will have a temperature gradient such that the coldest portion is underneath and the surface portion is the hottest. The floor of the pool will thus be solidified and will form a thermal insulating layer for the cylindrical wall 28 of the furnace. However, transition rim 25 will not have a large temperature gradient since the charge is relatively shallow when passing thereover. This rim should therefore be formed of a high temperature resistant and corrosion resistant ceramic.

Heat transfer from the flame 34 to the interior furnace wall is both radiative as well as conductive. Rotation of the wall around the stationary flame, together with the fluidizing gas flow pattern breaks up the laminar flow of the combustion gases which would otherwise act as an insulating, heat removing layer. The turbulent flow established in this manner is thus optimum for heat transfer. Any particles of the charge lost due to turbulent flow can be returned to charging hopper 32 by means of a cyclone separator (not shown) in the flue 38.

The flames 34 will have the required high temperature only in the reaction zone between transition rim 35 and weir 36, and this is a limited volume compared to the total volume of the flames. Care should thus be taken that the particles passing through the reaction zone require only a small enthalpy increase to be performed by the high temperature zone. It is inefficient to heat the charge from ambient temperature to the required high temperature using only high temperatures in the maximum temperature zone as is done in conventional practice. In the process of the present invention, the charge particles are preheated along the furnace wall by the colder parts of the flame and by the fluidizing gas. It is desirable to keep the temperature differential between the flames and the adjacent wall area to a minimum. These criteria dictate the speed of revolution of the rotating unit 27, the slope of the conical section 27 and the fluidizing conditions.

Impurities present in the coal and in the aluminum hydroxide will affect the process by reducing the amount of aluminum carbide formed and by generating undesired byproducts. However, the effects of some of the principal impurities resulting from combustion of coal are avoided in the process of the invention. In particular, sulfur oxides are not formed, and any nitrogen oxides which are formed are reduced in the furnace. Fly ash and other particulate impurities are not vented in the flue gas but are retained in the aluminum carbide. Substantially all the impurities remain in the sludge when the aluminum carbide is hydrolyzed and can be recovered as byproducts. The principal byproducts ordinarily would be sulfur, aluminum, iron, titanium, potassium and phosphorus. The degree of reduction of such elements from their normal oxide states would be determined by the maximum temperature, the temperature at which quenching is terminated and at which the product is exposed to air.

Sulfur present in low grade coal is an important consideration due to the necessity of avoiding sulfur oxides in combustion. Since the coal and aluminum oxide are heated to only to relatively low temperatures prior to their introduction into a reducing atmosphere of carbon monoxide and carbon dioxide, sulfur and other impurities are forced to compete with carbon for the relatively low level of oxygen which is present. The principal reactions are:

$C + \frac{1}{2}[O_2] \rightarrow CO$
$CO + \frac{1}{2}[O_2] \rightarrow CO_2$
hydrocarbons $+ O_2 \rightarrow 2H_2O +$ degraded hydrocarbons
$N_2 + [O_2]_x \rightarrow 2NO_x$
$2S + [O_2]_x \rightarrow 2SO_x$
where $x = 1$ or $2$ The reaction rates above are such that the hydrocarbons will deplete the available oxygen before $SO_x$ and $NO_x$ are formed. As the aluminum carbide is formed in the lower section of the furnace, the temperature is too high to form $SO_2$ or $SO$. As the aluminum carbide cools after discharge from the furnace, the reaction of carbon with oxygen to form carbon monoxide and carbon monoxide with oxygen to form carbon dioxide will dominate, leaving sulfur as a trace element in the carbide. During hydrolysis the sulfur remains in the residual sludge and can be recovered along with the other trace impurities.

We claim:
1. Apparatus for producing methane from aluminum hydroxide/aluminum oxide and coal, comprising means for supplying crushed coal; means connected to said supplying means for mixing crushed coal, aluminum hydroxide and a catalyst in predetermined proportions; a reduction furnace having means defining an inlet to receive the mixture of crushed cool, aluminum hyrdoxide and catalyst from said mixing means, said furnace including means for fluidizing and heating said mixture to a temperature of at least 1250° C. and means for collecting aluminum carbide formed therein, said means for fluidizing comprising means defining a rotating chamber having a conical fluidized bed preheat section in the upper portion of said furnace through which said mixture received in said inlet means passes downwardly, said rotating chamber having a cylindrical firebrick lining in the lower portion thereof receiving said mixture after preheating thereof in said fluidized bed preheat section, said furnace having means for rotating said chamber, burner means in the lower portion of said furnace for producing a stationary ring of flames in said lower portion, a transition rim around the inner periphery of said rotary chamber adjacent the upper end of said cylindrical lining, said means for collecting aluminum carbide formed in said furnace comprising a weir at the bottom of said lining for collecting a pool of molten reaction products, and means defining an outlet below said weir; means defining a quench chamber in communication with said outlet below said weir for receiving said aluminum carbide; means defining a hydrolysis chamber in communication with said quench chamber for receiving said aluminum carbide after quenching thereof, means in said hydrolysis chamber defining an inlet for water and/or steam, means in said hydrolysis chamber defining an outlet for withdrawal of methane-containing gas product, and means in said hydrolysis chamber defining an outlet for withdrawal of aluminum hydroxide and impurities in the form of a sludge; and means connected to said outlet for withdrawal of aluminum hydroxide for recycling aluminum hydroxide from said hydrolysis chamber to said mixing means.

2. The apparatus of claim 1, wherein said fluidized bed preheat section comprises a sloping wall having a plurality of apertures therein, means for introducing a heated reducing gas inwardly through said apertures, whereby rotation of said section results in turbulent flow of said reducing gas with consequent entrainment and preheating of said mixture of crushed coal, aluminum hydroxide and catalyst in said reducing gas.

3. The apparatus of claim 1, wherein said hydrolysis chamber is provided with a heat exchanger for control of the temperature therein.

4. The apparatus of claim 1, wherein said transition rim is formed from a ceramic material having high temperature and corrosion resistance.

5. In apparatus for producing methane from aluminum hydroxide/aluminum oxide and coal, including means for supplying a mixture of crushed coal, aluminum hydroxide and a catalyst, a reduction furnace connected to said supplying means, means defining a quench chamber in communication with said furnace, and means defining a hydrolysis chamber in communication with said quench chamber, the improvement wherein said reduction furnace has means defining an inlet to receive a mixture of crushed coal, aluminum hydroxide and a catalyst, means defining a rotating chamber having a fluidized bed preheat section in the upper portion through which said mixture received in said inlet passes downwardly and a firebrick lining in the lower portion thereof in communication with said preheat section, means for rotating said chamber, means in said furnace for heating said mixture to a temperature of at least 1250° C. in said lower portion of said chamber, means for collecting a pool of molten reaction products at the bottom of said lower portion, and means defining an outlet from said lower portion for discharge of said reaction products.

6. The improvement of claim 5, wherein said preheat section is conical and said lower portion is cylindrical, wherein said means for heating said mixture comprises burner means for producing a stationary ring of flames in said lower portion of said rotating chamber, and wherein said means for collecting a pool of molten reaction products comprises a weir having a rim which maintains a pool of reaction products having a depth sufficient to provide a temperature gradient wherein the lowermost colder portion is solidified.

7. The improvement of claim 6, including a transition rim around the inner periphery of said rotating chamber spaced shows above said weir.

8. The improvement of claim 7, wherein said transition rim is formed from a ceramic material having high temperature and corrosion resistance.

9. The improvement of claim 6, wherein said fluidized bed preheat section comprises a sloping wall having a plurality of apertures therein and means for introducing a heated reducing gas inwardly through said apertures, whereby rotation of said section results in turbulent flow of said reducing gas with consequent entrainment and preheating of said mixture therein.

10. The improvement of claim 9, wherein said means for introducing a heated reducing gas includes a conduit and compressor through which a portion of combustion gases formed by said flames is diverted.

* * * * *